United States Patent [19]
Shahinpoor et al.

[11] Patent Number: 6,109,852
[45] Date of Patent: Aug. 29, 2000

[54] SOFT ACTUATORS AND ARTIFICIAL MUSCLES

[75] Inventors: Mohsen Shahinpoor; Mehran Mojarrad, both of Albuquerque, N. Mex.

[73] Assignee: University of New Mexico

[21] Appl. No.: 09/101,856

[22] PCT Filed: Nov. 6, 1996

[86] PCT No.: PCT/US96/17870

§ 371 Date: Feb. 5, 1999

§ 102(e) Date: Feb. 5, 1999

[87] PCT Pub. No.: WO97/26039

PCT Pub. Date: Jul. 24, 1997

Related U.S. Application Data

[60] Provisional application No. 60/013,617, Jan. 18, 1996.

[51] Int. Cl.$^7$ .............................. B25J 15/00; B25J 17/00; B05D 5/12; B05D 7/04; A61M 25/09
[52] U.S. Cl. ......................... 414/1; 74/490.02; 244/213; 414/7; 427/341; 427/443.1; 604/171; 604/158; 604/177; 623/24; 623/25; 623/64
[58] Field of Search .......................... 74/490.02, 490.05; 244/22, 11, 72, 75 R; 395/80, 84; 427/308, 316, 337, 341, 342, 379, 434.2, 443.1; 414/753, 730; 901/1, 14, 16, 36; 623/25, 64; 604/158, 171

[56] References Cited

U.S. PATENT DOCUMENTS

| | | | |
|---|---|---|---|
| 4,083,765 | 4/1978 | Lawson | 204/195 W |
| 4,272,353 | 6/1981 | Lawrance | 204/283 |
| 4,328,086 | 5/1982 | Takenaka et al. | 204/296 |
| 4,364,803 | 12/1982 | Nidola et al. | 204/30 |
| 4,417,959 | 11/1983 | Kadija et al. . | |
| 4,449,599 | 5/1984 | Creek . | |
| 4,496,451 | 1/1985 | Ishii et al. . | |
| 4,522,598 | 6/1985 | Maget . | |
| 4,537,910 | 8/1985 | Oogai et al. . | |
| 4,546,010 | 10/1985 | Killer et al. . | |

(List continued on next page.)

OTHER PUBLICATIONS

Asaka, K., et al., "Bending of Polyelectrolyte Membrane—Platinum Composites by Electric Simulli I. Response characteristics to Various Waveforms," *Polymer Journal*, vol. 27, No. 4, pp. 436–440 (1995).

Burroughs, C., "UNM's Muscle Research," *Albuquerque Business Times*, Nov. 11–25, 1996.

Millet, P., et al., "Preparation of Solid Polymer Electrolyte Composites: Investigation of the Ion–Exchange Process," *Journal of Applied Electrochemistry*, vol. 25, pp. 227–232, 233–239 (1995).

Millet, P., et al., "New Solid Polymer Electrolyte Composites for Water Electrolysis," *Journal of Applied Electrochemistry*, vol. 19, pp. 162–166 (1989).

Millet, P., et al., "Preparation of New Solid Polymer Electrolyte Composites for Water Electrolysis," *Int. J. Hydrogen Energy*, vol. 15, No. 4, pp. 245–253 (1990).

(List continued on next page.)

*Primary Examiner*—Diana Dudash
*Attorney, Agent, or Firm*—Jeffrey D. Myers; Andrea L. Mays; Dickson G. Kehl

[57] ABSTRACT

A chemical (coating and reduction)/mechanical/electrical treatment of ion-exchange materials (preferably ion-exchange membranes) to convert them to artificial muscles. The figure is a perspective view of an actuator of the invention showing the treated membrane actuator (A) with electrodes (25 and 26) placed at one end of the membrane, the electrodes being further attached to a power source (35). Artificial muscles created by the inventive method are capable of undergoing electrically-controllable large deformations resembling the behavior of biological muscles. A typical flap muscle of 0.2–0.4 mm thickness, 2–5 mm width and 20 mm length manufactured by the inventive process can achieve a completely reversible maximum deflection of 12–15 mm under a maximum voltage of 2.0–2.5 volts.

11 Claims, 7 Drawing Sheets

U.S. PATENT DOCUMENTS

| | | |
|---|---|---|
| 4,565,487 | 1/1986 | Kroczynski . |
| 4,578,045 | 3/1986 | Mayer . |
| 4,681,855 | 7/1987 | Huang ........................................ 436/39 |
| 4,717,581 | 1/1988 | Robblee ................................. 427/2.12 |
| 4,748,737 | 6/1988 | Charles et al. . |
| 4,818,353 | 4/1989 | Langer et al. . |
| 4,835,395 | 5/1989 | McManus et al. ...................... 250/435 |
| 4,858,063 | 8/1989 | Laue et al. .............................. 361/286 |
| 4,919,891 | 4/1990 | Yafuso et al. ......................... 427/2.12 |
| 4,940,318 | 7/1990 | Ealy et al. .............................. 350/611 |
| 4,959,132 | 9/1990 | Fedkiw, Jr. . |
| 5,038,821 | 8/1991 | Mget . |
| 5,062,841 | 11/1991 | Siegel ................................... 604/891.1 |
| 5,089,659 | 2/1992 | Yim et al. .............................. 427/2.12 |
| 5,100,933 | 3/1992 | Tanaka et al. . |
| 5,109,813 | 5/1992 | Ohashi et al. . |
| 5,250,167 | 10/1993 | Adolf et al. . |
| 5,268,082 | 12/1993 | Oguro et al. ............................ 204/282 |
| 5,275,820 | 1/1994 | Chang ................................... 427/2.12 |
| 5,279,559 | 1/1994 | Barr . |
| 5,334,304 | 8/1994 | Maget ..................................... 204/421 |
| 5,389,222 | 2/1995 | Shahinpoor . |
| 5,471,185 | 11/1995 | Shea et al. ................................ 335/51 |
| 5,481,152 | 1/1996 | Baschulte ................................ 310/328 |
| 5,529,279 | 6/1996 | Beatty et al. ............................. 251/11 |
| 5,531,664 | 7/1996 | Adachi et al. . |
| 5,554,272 | 9/1996 | Benco et al. ......................... 205/782.5 |
| 5,556,700 | 9/1996 | Kaneto et al. . |
| 5,614,246 | 3/1997 | Mund et al. ........................... 427/2.24 |
| 5,685,837 | 11/1997 | Horstmann ............................. 427/2.12 |

OTHER PUBLICATIONS

Mojarrad, M., et al., "Ion–Exchange–Metal Composite Sensor Films," *SPIE*, vol. 3042 (1997).

Oguro, K., et al., "Polymer Film Actuator Driven by a Low Voltage," $4^{th}$ Int'l Symp on Micro and Human Science, Jagiya, Japan (1993) pp. 39–40.

Sadeghipour, et al., "Development of a Novel Electrochemically Active Membrane and 'Smart' Material Based Vibration Sensor/Damper," *Smart Materials Struc*, vol. 1, pp. 172–179 (1992).

Furlow, B., "(Muscle) Bound for Glory", *Mirage–University of New Mexico*, Spring 1997.

Shahinpoor, M., "The Ionic Flexogelectric Effect in Polymeric Gels" *School of Engineering UNM* (1996).

SOFT ACTUATORS AND ARTIFICIAL MUSCLES

CROSS-REFERENCE TO RELATED APPLICATIONS

This application claims the benefit of the filing of Provisional Application Ser. No. 60/013,617, entitled Method of Manufacturing and Applications of Electrically Controllable Artificial Muscles from Polymeric Ion-Exchange Membranes, filed on Jan. 18, 1996.

BACKGROUND OF THE INVENTION

1. Field of the Invention

The present invention relates to a novel method of manufacturing actuators, e.g., artificial muscles, and novel applications of the actuators manufactured according to the novel method. More particularly, the invention relates to a novel chemical/mechanical/electrical treatment of membranes, e.g. ion-exchange membranes, to convert them to artificial muscles capable of undergoing electrically-controllable large deformations resembling the behavior of biological muscles. The invention further relates to a number of novel techniques for packaging and application of the said artificial muscles.

2. Background Art

The creation of controllable actuators, or synthetic muscles, is known. Artificial muscles or actuators made from ion-exchange membranes are relatively new but also known.

U.S. Pat. No. 4,522,698, to Maget, discloses a prime mover that uses pressure increases and decreases induced by converting molecules of electrochemically active material to ions, transporting ions through an electrolytic membrane and reconverting the ions to molecules. The prime mover includes gas-tight compartments filled with an electrochemically active material and separated by an electrolytic membrane, such as an ion-exchange membrane, that incorporates electrodes so that a voltage gradient can be established across the membrane to induce current flow through the membrane. When the current flows through the membrane, molecules travel through the membrane and are reconverted to molecules in the opposite compartment causing a pressure increase in the receiving compartment and a pressure decrease in the other compartment. The pressure changes are converted to mechanical motion which can be used as a driver for a mechanical load. The disadvantages of this technique are that the resulting motion is small and the pressure increase may rupture the membrane.

U.S. Pat. No. 5,100,933, to Tanaka, et al., discloses the use of ionized cross-linked polyacrylamide gels as engines or artificial muscles; the gels can contain a metal ion and are capable of discontinuous volume changes induced by infinitesimal changes in environment. The gel is made by dissolving acrylamide monomers and bisacrylamide monomers in water, adding a polymerization initiator (in particular, ammonium persulfate and TEMED, or tetramethyl-ethylene-diamine) to the solution, soaking the gel sample in water to wash away all residual monomers and initiators, immersing the gel in a basic solution of TEMED for up to 60 days, then immersing the gel in a solvent (in particular, acetone, acetone in water, ethanol and water, or methanol and water). The primary disadvantages of these actuators are generally that the response time of the gel is much longer than that of other known actuator components and that the gel must be contained in the solvent bath. The gels are also mechanically brittle and easily broken.

U.S. Pat. No. 5,250,167, to Adolf, et al., discloses actuators or synthetic muscles, using polymeric gels contained in compliant containers with their solvents; these actuators undergo substantial expansion and contraction when subjected to changing environments. The actuators may be rigid or flexible and may be computer-controlled. The driver may also be electrolytic, where application of a voltage across the polymer gel causes a pH gradient to evolve between the electrodes. For example, filling the polymer fibers with platinum by alternatively treating them with solutions of platinic chloride and sodium borohydride obtains a reversible expansion and contraction of the fiber with the application of an electric field. The actuating gel itself is the only moving part required and the electric field may be only on the order of a few volts per centimeter. The disadvantage is that actuator performance is dictated by the parameters of the polymeric gel used. Furthermore, liquid containment is required to make the actuators stronger and not so easily broken.

U.S. Pat. No. 5,389,222, to Shahinpoor, discloses electrically controllable polymeric gel actuators or synthetic muscles, using gels made of polyvinyl alcohol, polyacrylic acid, polyacrylonitrile, or polyacrylamide contained in an electrolytic solvent bath. These actuators operate by reacting to changes in the ionization of a surrounding electrolyte by expanding or contracting, and can be spring-loaded and/or mechanically biased for specific applications. Polymeric gel configurations such as sheets, solid shapes or fiber aggregates are contemplated, as are the use of a salt water solution for the electrolyte, and a platinum catalyst if) the actuator housing to recombine the hydrogen and oxygen produced as a result of electrolysis during ionization of the electrolyte. Again, liquid containment is required to maintain strength and electric controllability, and not enough deformation or displacement is generated.

Thus, there is an existing need for a soft actuator that performs activation noiselessly and efficiently (as do biological muscles) with a low ratio of mass to power or a high ratio of power or force to mass.

SUMMARY OF THE INVENTION (DISCLOSURE OF THE INVENTION)

In view of the above-described needs, it is a primary object of this invention to provide a soft activation means resembling biological muscles.

The limitations associated with existing actuators and the methods for their manufacture are overcome by the present invention which provides a method of preparing actuators (synthetic muscles) comprising the steps of: rinsing an ion-exchange material; coating the ion-exchange material with a substance which undergoes chemical reduction in the presence of a reducing agent; and reducing the coating on the ion-exchange material by exposing the ion-exchange material to a reducing agent. In the preferred embodiment, the ion-exchange material comprises a material selected from the group consisting of ion-exchange membranes, ionomer membranes, ion-exchange resins, gels, beads, powders, filaments, and fibers, preferably an ion-exchange membrane, more preferably a polymer ion-exchange membrane, and most preferably a perflourinated sulfonic acid ion-exchange polymer membrane. Rinsing is best performed in water. The ion-exchange material preferably has at least two surfaces and rinsing is preceded by roughening the surfaces of the ion-exchange material, such as by sandblasting with fine glass bead sandblast. Rinsing is also preferably preceded by cleaning the ion-exchange material in an ultrasonic water bath cleaner. The cleaning includes heating (preferably boiling) the ion-exchange material in solution (preferably acidic, most preferably HCl). Most preferably, the ion-exchange material has at least two surfaces and rinsing comprises (in order): roughening the surfaces of the ion-exchange material; cleaning the ion-exchange material; rinsing the ion-exchange material in water; and boiling the ion-exchange material in an aqueous solution (preferably acidic, such as an HCl solution). Rinsing preferably comprises at least two steps of rinsing and boiling the ion-exchange material in solution (in water, for a sufficient time to completely swell the ion-exchange material). Coating is preferably done with a metal, more preferably a noble metal and most preferably with platinum, and is performed for a time sufficient to cover the ion-exchange material with a coating of approximately 3.75 mg/cm$^2$ of the coating substance. Coating best comprises: immersing the ion-exchange material; and stirring. Immersing is preferably done into a solution containing a salt of a metal, such as a noble metal, palladium, or nickel, preferably a platinum salt, more preferably a platinum-amine complex, and most preferably $Pt(NH_3)_4Cl_2$. The reducing step best comprises exposing the ion-exchange material to $NaBH_4$. Reducing is preferably done in solution (e.g., aqueous) containing a reducing enhancer such as $NH_4OH$, and involves continuously raising the temperature of the solution to a predetermined temperature. Reducing is best done at an elevated temperature in solution in a water bath at an elevated temperature and includes simultaneously stirring the solution in the water bath, and preferably simultaneously stirring the solution (at low speed) while adding the reducing agent. Most preferably, reducing comprises simultaneously: continuously raising the temperature of the solution to a predetermined temperature; and adding supplementary reducing agent at intervals. This preferably includes maintaining the temperature at the predetermined temperature and simultaneously adding a final amount of supplementary reducing agent when the predetermined temperature is reached, continuously stirring the solution after adding the final amount of supplementary reducing agent, rinsing the ion-exchange material (in water or HCl solution), and storing the ion-exchange material. Preferably, the reducing step comprises at least one reducing step comprising (in order): rinsing the ion-exchange material; immersing the ion-exchange material in a solution containing a reducing agent; rinsing the ion-exchange material and storing the ion-exchange material. Preferably, the immersing is in a solution (aqueous) containing a salt of a metal such as a noble metal, palladium, or nickel, preferably a platinum salt, more preferably a platinum-amine complex, and most preferably $Pt(NH_3)_4Cl_2$, as well as a reducing enhancer such as $NH_4OH$, as well as a reducing agent such as $H_2NOH \cdot HCl$ or $H_2NNH_2 \cdot H_2O$. Reducing preferably comprises simultaneously: continuously raising the temperature of the solution to a predetermined temperature; and adding supplementary reducing agent at regular intervals for a time sufficient to substantially complete reduction, as well as testing the solution for completion of reduction such as by monitoring a color change produced by reduction. Rinsing preferably involves at least two rinsing steps, the first in water or an acidic (HCl) solution, or both in sequence, and is performed for a time sufficient to exchange cations in the ion-exchange material for H+ cations outside the ion-exchange material. The second is in water or a basic (NaOH) solution, or both in sequence, and is performed for a time sufficient to exchange cations in the ion-exchange material, such as H+ cations in the ion-exchange material are exchanged for alkali metal (Na+) cations outside the ion-exchange material. Preferably, a second of the at least one reducing and the rinsing are repeated, followed by a final rinsing step in water. After the two preferred rinsing steps, the ion-exchange material is preferably cleaned ultrasonically. Storing is preferably done in water.

The invention is also of a method of preparing an actuator comprising: at least one cleaning step; at least one step of rinsing an ion-exchange material; at least one step of coating the ion-exchange material with a substance which undergoes chemical reduction in the presence of a reducing agent; at least one step of reducing the coating on the ion-exchange material by exposing the ion-exchange material to a reducing agent; testing the solution for the completion of reduction; and at least one step of storing the treated ion-exchange material. In the preferred embodiment, the ion-exchange material is an ion-exchange membrane, an ionomer membrane, an ion-exchange resin, a gel, beads, a powder, filaments, or fibers, preferably an ion-exchange membrane, more preferably a polymer ion-exchange membrane, and most preferably a perfluorinated sulfonic acid ion-exchange polymer membrane. Rinsing is preferably done in water or solution (acidic, such as HCl, or basic, such as NaOH), and involves heating (boiling in solution) the ion-exchange material. At least two rinsings are best performed before coating. Coating is preferably done with a metal, preferably a noble metal, palladium, or nickel, and most preferably platinum. Preferably, at least one rinsing occurs before and after each reducing, and the reducing is done in the presence of a reducing enhancer ($NH_4OH$). Exposing is best done to a reducing agent ($NaBH_4$, $H_2NOH \cdot HCl$, or $H_2NNH_2 \cdot H_2O$), preferably first to $NaBH_4$, and later to $H_2NOH \cdot HCl$ or $H_2NNH_2 \cdot H_2O$. Preferably, reducing is done in solution and includes: heating the reducing solution; continuously stirring the ion-exchange material in the coating solution at low speed; and simultaneously raising the temperature of the solution while adding supplementary reducing agent. Testing preferably includes: mixing a test solution comprising a portion of the reducing solution; boiling the test solution; and detecting a color change in the testing solution during boiling. The portion is preferably about 2 ml and testing includes: adding $NaBH_4$ to the test solution during boiling; and adding supplemental reducing agent to the reducing solution in which the ion-exchange material is immersed if a coloration is detected in the test solution during boiling, and terminating reducing otherwise. Storing is best done in water or in solution (acidic, such as HCl).

The invention is additionally of a method of preparing an actuator from an ion-exchange material comprising: roughening the ion-exchange material; a first step of cleaning the roughened ion-exchange material; a first step of rinsing the ion-exchange material; a first step of boiling the ion-exchange material; a second step of rinsing the ion-exchange material; a second step of boiling the ion-exchange material wherein boiling is performed for a sufficient time to completely swell the ion-exchange material; a step of coating the ion-exchange material with a substance comprising platinum: a third step of rinsing the ion-exchange material; a first step of reducing the coating on the ion-exchange material by immersing the coated ion-exchange material in a solution comprising a reducing agent whereby the coating undergoes chemical reduction in the presence of the solution comprising the reducing agent; simultaneously heating and stirring the ion-exchange material in the reducing agent; a fourth step of rinsing the ion-exchange material; a first step of storing the ion-exchange material; a fifth step of rinsing the ion-exchange material; a second step of reducing the coating on the ion-exchange material by immersing the coated ion-exchange material in a solution comprising a reducing agent whereby the coating undergoes chemical reduction in the presence of the solution comprising the reducing agent; simultaneously heating and stirring the ion-exchange material in the reducing agent; at least one step of sequentially rinsing the ion-exchange material; a second step of cleaning the ion-exchange material; and a second step of storing the ion-exchange material. The steps are preferably performed in the above order, and the last four repeated and including a final rinsing step prior to the second storing step.

The present invention is also of an actuator, produced by any of the above summary methods, comprising a treated ion-exchange material capable of a completely reversible deflection and means operably connected to the ion-exchange material for electrically driving the deflection of the ion-exchange material.

The invention is further of an actuator for use in a gripper mechanism comprising: at least two actuators, produced by any of the above methods, positioned opposite to each other and being capable of bending in equal and opposing directions; a power supply to the actuators to drive the mechanical bending of the actuators in opposing directions; electrical impulse conductors operably attached to the first end of each of the actuators for conducting electrical impulses across the actuators; and wiring, operably attached to the conductors and to the power supply, for electrically connecting the actuators to the power supply.

The invention is additionally of an actuator for providing three-dimensional movement, comprising: three actuators produced by any of the above methods, comprising a hollow triangular tube having a longitudinal axis wherein each of the actuators of the tube comprises a face of the tube; signal conductors, operably attached to the first end of each of the actuators, for conducting a signal across each of the faces of the tube, thereby stimulating each face of the tube at a phase angle apart from each adjacent face to produce a motion around the longitudinal axis of the tube; and a power supply for providing power to the signal conducting means; and a power conductor, attached to the signal conductors, for operably connecting the tube to the power supply. The signal is preferably a low amplitude alternating signal.

The present invention is still further of an actuator for use as a wing flap, comprising: at least two actuators, produced by any of the above methods, sandwiched in series in a stack configuration each of the actuators formed in a planar layer and capable of acting as a series resistor element; power conductors, operably attached to the stack at the first end and the top and bottom surfaces, for conducting power across the stack; a power supply for supplying power to the stack; and connectors for connecting the power supplying means to the power conducting means. In the preferred embodiment, adhesive is placed between the actuators, preferably conductive and non-continuously applied.

The invention is also of an actuator for use as a robotic swimming structure, comprising: at least two actuators produced by any of the above methods, formed in an ion-exchange material having a first end, the ion-exchange material comprising a plurality of polymer gel fibers imprinted with means for conducting power through the ion-exchange material; conductors, operably attached to the ion-exchange material at the first end, for conducting an alternating low voltage across the ion-exchange material; a power supply for providing power to the conductors; a modulator for modulating speed of bending of the ion-exchange material varying the frequencies of the applied voltage; and a connector for operably connecting the conducting means to the power providing means. In the preferred embodiment, the actuator includes a buoyancy varier for varying the buoyancy of the swimming structure and a sealed housing, operably attached to the ion-exchange material at the first end, the housing comprising a signal generator (erasable programmable chip) and a power generator (a battery). The ion exchange material may be elastic or rigid.

The invention is yet further of an actuator for use as a resonant flying machine, comprising: at least one ion-exchange material actuator, prepared by any of the above methods, in the form of a planar layer having first and second ends, a top surface and a bottom surface; power conductors for conducting power across the ion-exchange material actuator, operably attached to the top and bottom surfaces of the ion-exchange material and along a central axis of the ion-exchange material equidistant from the first and second ends, whereby the ion-exchange material actuator is capable of reversibly bending in a flapping motion upon receiving power; a power supply for providing power to the conductors; and connectors for connecting the conductors to the power supply.

The invention is also of an actuator for use as a guide wire or a micro-catheter in intra-cavity medical applications, comprising: at least one ion-exchange material actuator prepared by any of the above methods, and formed in a small strip; a power supply for providing power to the strip; and connectors for connecting the strip to the power supply.

The invention is also of a sphincter-type or a squeeze-type actuator used in medical applications for incontinence and cardiac-assist devices.

Additional objects, advantages and novel features, and further scope of applicability of the present invention will be set forth in part in the detailed description to follow, taken in conjunction with the accompanying Figures, and in part will become apparent to those skilled in the art upon examination of the following detailed description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying Figures, which are incorporated into and form a part of the specification, illustrate several embodiments of the present invention and, together with the description, serve to explain the principles of the invention. However, these Figures, as well as the following detailed description and the examples, are only for the purpose of illustrating a preferred embodiment of the invention and are not to be construed as limiting the invention. In the drawings.

Figure 1:
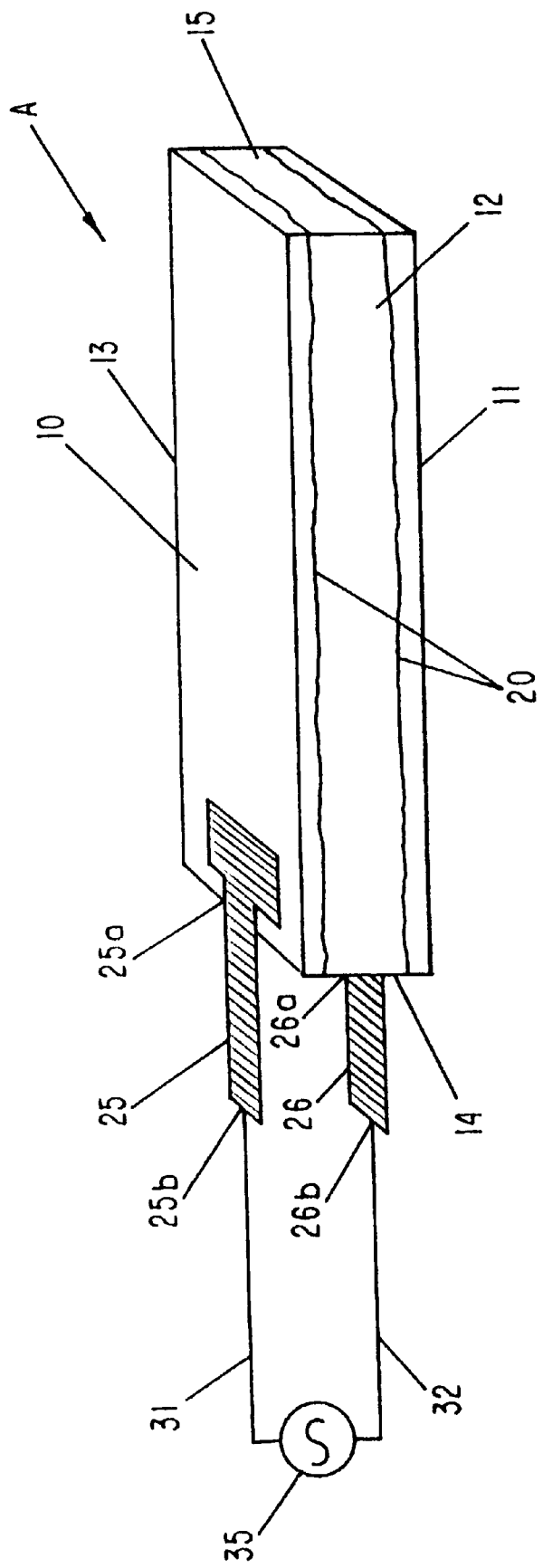
FIG. 1 is a perspective view of the actuator of the invention showing the treated membrane actuator with electrodes placed at one end of the membrane and terminals connected to a power source at the other end.

DESCRIPTION OF THE REFERRED EMBODIMENTS (BEST MODES FOR CARRYING OUT THE INVENTION)

The invention involves methods of manufacturing, packaging and use of ion-exchange membrane actuators made from ion-exchange membranes (or any ionomer membrane, ion-exchange resin, gel, beads, powder, filaments, or fiber) by chemically, mechanically and electrically treating them with at least one noble metal such as platinum.

A method of the invention of preparing an actuator comprises rinsing a membrane, coating the membrane with a substance which undergoes chemical reduction in the presence of a reducing agent, reducing the coating on the membrane by exposing the membrane to a reducing agent. The proposed manufacturing technique produces a typical flap muscle of 0.2–0.4 mm thickness, 2–5 mm width and 20 mm length which can achieve a completely reversible maximum deflection of 12–15 mm under a maximum voltage of 2.0–2.5 volts. More particularly, in the method for manufacturing actuators according to the subject invention, electrically controllable artificial muscles are produced from polymeric ion-exchange membranes by a method comprising a first cleaning step, at least one step (preferably two steps) of rinsing a membrane, at least one step of coating the membrane with a substance which undergoes chemical reduction in the presence of a reducing agent, at least one step (preferably two steps) of reducing the coating on the membrane by exposing the membrane to a reducing agent, a second cleaning step, and at least one step (preferably two steps) of storing the treated membrane. Several of these steps, in particular the reducing steps, may be repeated as needed to obtain a desired result.

The invention also includes a number of novel applications, devices and actuators made from this specially treated material. Preferred uses of the treated membrane of the invention include any application requiring noiseless propulsion in water. Further applications include its use as a gripper (tweezers), an three dimensional actuator for use with a generator, a composite wing flap, an autonomous robotic swimming structure, a resonant flying machine, a snake-like robot, a wobble motor, and a multi-fingered robotic hand.

The present invention having been generally described, the following preferred specific embodiments are provided to illustrate some of the properties and demonstrate the practical advantages thereof, and to allow one skilled in the art to utilize the present invention to its fullest extent. These examples included are to be construed as merely illustrative, and not limitative of the remainder of the disclosure or the claims in any way whatsoever.

The manufacturing method of the present invention was performed using ion-exchange membranes (or any ionomer membrane) such as a perflourinated sulfonic acid polymer or ionomer such as Nafion™ (Dupont deNemours & Company trademark) which is a perfluorinated sulfonic acid ion-exchange polymer membrane are used for separation processes, production of caustic sodas and fuel cell application in the industry. Ion-exchange membranes are hydrophilic ionic polymers and swell up to 16% in water at room temperature.

The following lists the step-by-step preparation of an exemplary actuator from a 2 by 2 square inch Nafion™ 117 membrane (0.007 inch thick):

1. Both surfaces of the membrane are roughened using a smooth sandpaper (such as Norton 600A). Alternatively, roughening can be accomplished with short bursts of fine glass bead sandblast (2 sec/cm$^2$).

2. The membrane is then cleaned in an ultrasonic water bath cleaner for about 10 minutes.

3. The membrane is rinsed with pure (deionized) water and boiled in a 2.4N aqueous solution of HCl for about 30 minutes.

4. The membrane is again rinsed with pure water and boiled in pure water for about 30 minutes to completely swell the membrane.

5. The membrane is then immersed in a solution of 0.2% platinum-amine complex ($Pt(NH_3)_4Cl_2$) (tetra-amine platinum chloride hydrate, 98%) for 8 hours at room temperature while slowly stirring the solution. The final amount of platinum deposited on the membrane must be about 3.75 mg/sq cm for each face of the membrane surface. This produces a pair of porous dendrilic electrodes on the surface of the membrane.

6. The membrane is then rinsed again with pure water and immersed in a reducing solution consisting of 180 ml $H_2O$, 0.5 ml $NH_4OH$ 30%, and 2 ml $NaBH_4$ 5% in a water bath at 40° C. while stirring al low speed (150 RPM). Additions of 2 ml $NaBH_4$ 5% are made every 30 minutes for about 3 and a half hours while gradually raising the temperature to 60° C., at which point 20 ml $NaBH_4$ 5% is added, and the mixture is stirred for an additional one and a half hours. Then the membrane is rinsed with pure water and stored in a 0.5% solution of HCl for 8 hours.

7. Following its removal from storage, the membrane is again rinsed with pure water and immersed in a solution containing 300 ml $H_2O$, 0.2 grams $Pt(NH_3)_4Cl_2$, 3 ml $H_2NOH \cdot HCl$ 5% (hydroxylamine hydrochloride, 99%), 1.5 ml $H_2NNH_2 \cdot H_2O$ 20% (hydrazine monohydrate, 98%), and 0.5 ml $NH_4OH$ 30% at 40° C. while stirring at low speed (approximately 60 RPM). Reducing agents consisting of 3 ml $H_2NOH \cdot HCl$ 5% and 1.5 ml $H_2NNH_2 \cdot H_2O$ 20% were then added every 30 minutes for 4 hours while gradually increasing the temperature to 60° C. After the process is over, the solution containing the membrane was tested for any residual Pt by boiling 2 ml of the solution with 2 ml $NaBH_4$ 5%. If the color of the mixture turns black, the addition of reducing agents must continue for longer time. If no color change is visually detected, the process is complete. Step 7 is part of the developing process to deposit more platinum in the polymer matrix.

8. When reduction is complete, the membrane is rinsed with pure water and then with 0.1N HCl solution to remove any other cations in the membrane. Steps 7 and 8 are necessary to insure high level of activity in the final actuator.

9. The membrane is rinsed again with pure water and then with 0.1 N NaOH solution to replace H+ cations in the membrane with Na+ cations.

10. The membrane is then cleaned in an ultrasonic cleaner for 5 seconds and removed.

11. Steps 7, 8, and 9 are repeated and followed by rinsing with pure water. The membrane is then stored in pure water at room temperature. Step 10 repeats the developing process to increase the amount of platinum deposited. If one starts out with a higher concentration of platinum salt in step 7, it is possible to deposit sufficient platinum on the membrane on the first pass, thereby eliminating the need for step 11. However, this will increase the risk of oxidation as well as crowding phenomena on surfaces of the membrane in a short time period.

A flap muscle with dimensions of 0.2–0.4 mm thickness, 5 mm width and 40 mm length is typically cut from sheets of 100 mm×150 mm membrane muscles produced by the performance of the above-described steps. This muscle can achieve a completely reversible maximum deflection of 22–25 mm under a maximum voltage of 2.0–2.5 volts and provides noticeable power to weight ratio at low voltages to perform useful work. A major advantage is that one can cut any shape and size muscle from the sheet. In particular, micro-muscles in down to approximately 200 microns in length and 40 microns in width may be cut from such sheets.

FIG. 1 depicts such an actuator made by chemically and mechanically treating Nafion™ membranes with platinum according to the method of the invention. FIG. 1 is a perspective view of a treated membrane actuator A in planar form comprising a top surface 10, bottom surface 11 (not shown), sides 12 (shown) and 13 (not shown), a first end 14 (not shown) and a second end 15. As shown, electrodes 20 extend through sides 12 and end 15. Preferably, electrodes 20 are platinum. At end 14, terminals 25 and 26 are attached at their first ends 25a and 26a, respectively, to top surface 10 and bottom surface 11 of actuator A. Terminals 25 and 26 at their second ends 25b and 26b, respectively are connected by wires 31 and 32, respectively, to a power source 35.

Membrane actuators can be manufactured and packaged for specific applications. These actuators produce a bending motion when placed in a low voltage electric field. The membrane always bends toward the anode and then back to cathode and null position when a low voltage is applied and removed sequentially. The bandwidth of the membrane depends on its size and geometry; for the typical actuator, the bandwidth is about 40 Hz. Also, for the typical actuator produced by the method above, the current across the membrane is about 100 mA/sq cm, and the applied voltage necessary for actuation is about 1.5–2.5 volts. The most important aspect here is to chemically deposit (or coal) porous (perforated) platinum electrodes on the membrane surface with some penetration inside the membrane across its thickness. For purposes of the specification and claims, "coating" is defined as depositing a layer (porous or non-porous), when used as a verb, and as a deposit (porous or ion-porous), when used as a noun.

The actuators of the invention are hydrophilic and operate in moist environments. Therefore, for application in open-air systems, they are preferably encapsulated in an elastic membrane such as latex.

Industrial Applicability:

The invention is further illustrated by the following non-limiting examples.

The following examples are additional embodiments of the present invention and illustrate novel applications of the artificial muscles and actuators resulting from experiments using the method of manufacturing of the subject invention.

EXAMPLE 1

Membrane Grippers

Figure 2:
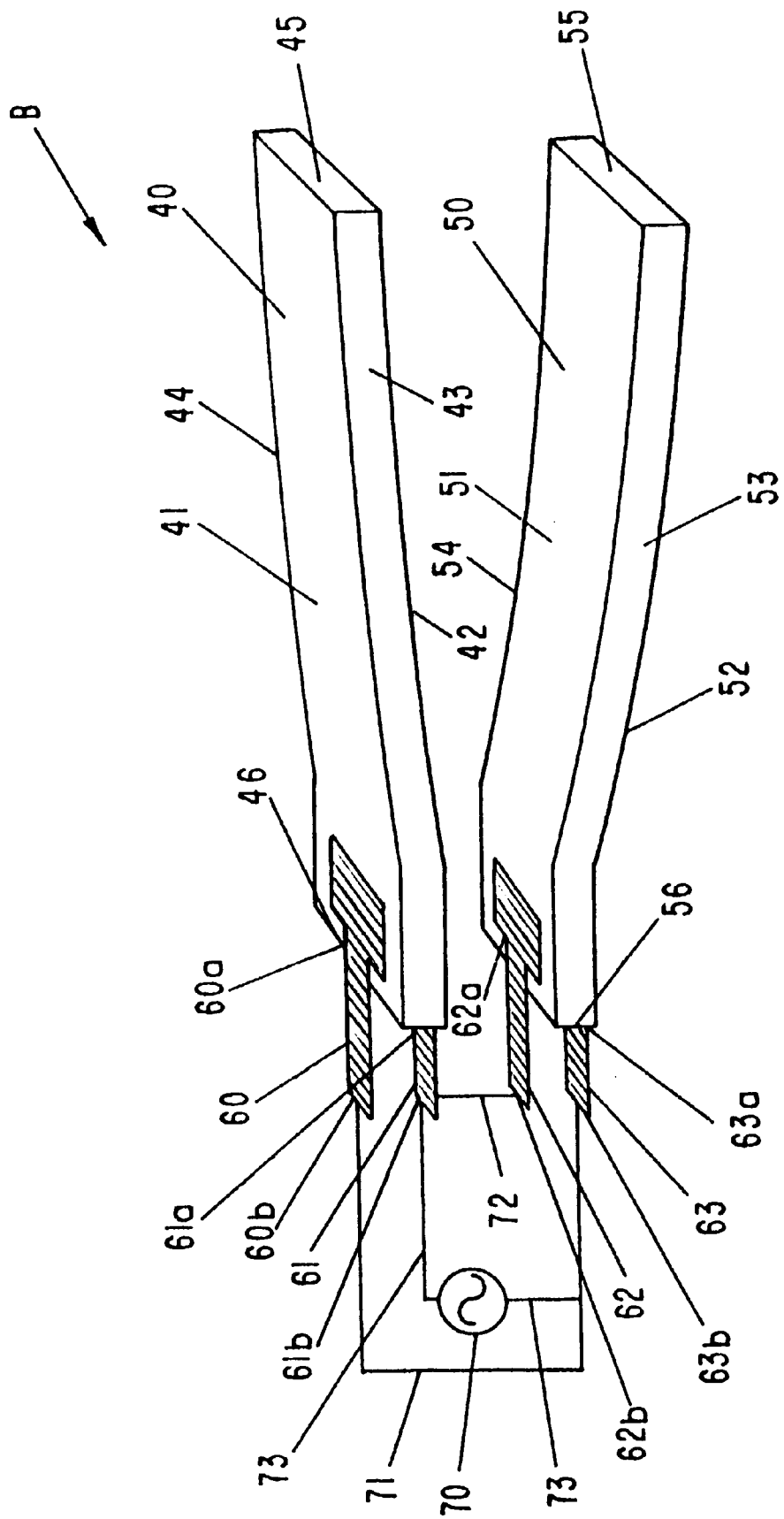
FIG. 2 is a perspective view of the actuator of the invention showing use of the treated membrane actuator as an electrically controlled tweezer with terminals connected to a power source at one end.

The membrane can be fabricated to act as a micro- or macro-gripper, e.g., tweezers, for gripping action when two membranes are wired and sandwiched in a way so that they bend in opposing direction. FIG. 2 is a perspective view of an embodiment of the invention showing two treated membrane actuators 40 and 50 packaged as an electrically controlled gripper B. Actuators 40 and 50 each comprise respectively top surfaces 41 and 51, bottom surfaces 42 and 52 (not shown), sides 43 and 53 (shown), sides 44 and 54 (not shown), first ends 45 and 55 (shown) and second ends 46 and 56 (not shown). Actuators 40 and 50 are disposed opposite to each other with bottom surface 42 of actuator 40 facing top surface 51 of actuator 50. The first ends 60a and 61a of terminals 60 and 61 are attached to the top surface 41 and the bottom surface 42, respectively, at the second end 46 of actuator 40, and the first ends 62a and 63a of terminals 62 and 63 are attached to the top surface 51 and the bottom surface 52, respectively, at the second end 56 of actuator 50. Terminals 60 and 63 are connected to each other and to one pole of the power supply 70 by electrical wire 71 attached to their ends 60b and 63b, respectively. Terminals 61 and 62 are connected to each other by electrical wire 72 attached to their ends 61b and 62b, and to the other pole of the power supply 70 by electrical wire 73, respectively. The length of wire 72 depends on the required gap between the two actuators 40 and 50 depending on application.

EXAMPLE 2

Three-dimensional Membrane Actuator

Figure 3:
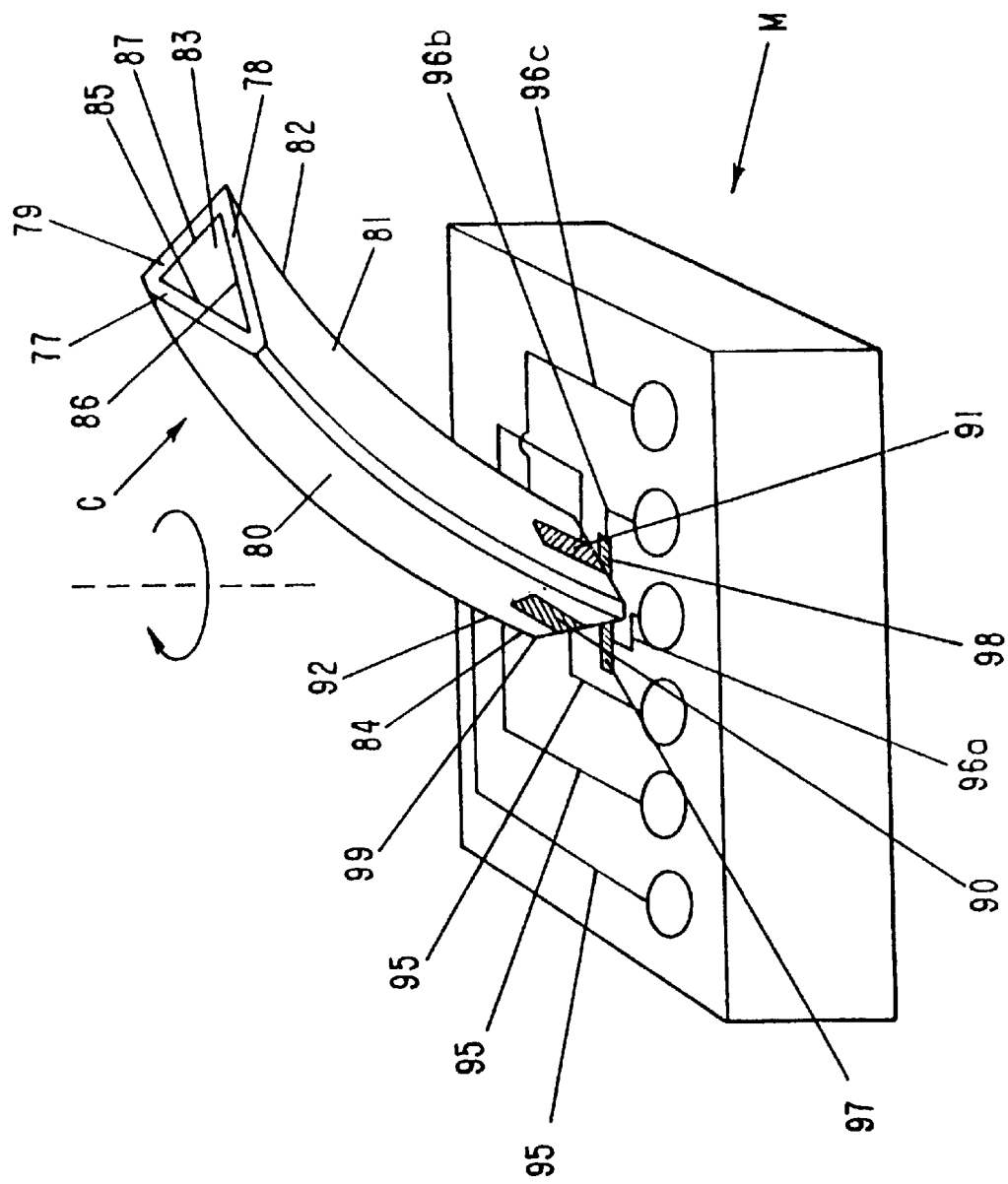
FIG. 3 is a perspective view of the actuator of the invention showing the treated membrane actuator packaged in three dimensional form for use with a three-phase generator box. Terminals are disposed at the end of the actuator positioned nearest the generator box.

FIG. 3 is a perspective view of a three-dimensional membrane actuator C packaged in three-dimensional form for use with a three-phase generator box M. Actuator C comprises a hollow triangular tube configuration consisting of three independent membrane actuators 77 (shown), 78 (shown) and 79 (partially shown) attached and electrically insulated along the long edges with three external faces 80 (shown), 81 (shown) and 82 (not shown), respectively and a first end 83 (free) and second end 84 which is fixed to the generator box M. External terminals 90 (shown), 91 (shown), and 92 (not shown) are disposed at the second end 84 of actuator C for connection to electrodes 95a (shown), 95b (shown), 95c (shown), respectively incorporated in generator box M. Internal faces of the actuators 85 (not shown), 86 (not shown), and 87 (shown) are connected via internal terminals 97 (partially shown), 98 (partially shown) and 99 (not shown) to electrodes 96a (shown), 96b (shown) and 96c (shown) of the generator box M, respectively Membrane actuator C is fabricated to produce a 3-dimensional movement by positioning each of actuators 77, 78, and 79 to be stimulated at a phase angle apart from the adjacent actuator by a low amplitude alternating signal, therefore inducing wobble-like motion around the long imaginary axis of the combined actuator tube in null position.

In FIG. 3, the three actuators 77, 78, and 79 are joined together by a flexible adhesive (such as LOCTITE SUPERFLEX™) at the edges (seams). Each actuator has its own terminal connections to each phase of a typical 3-phase power generator (M) or a multi-phase power supply (programmable function generators/power supplies exist that have phase-separated outputs). Each of these actuators has its external and internal faces similar to the top and bottom faces of the tweezer shown in FIG. 2. The final actuator, then, looks like a triangular hollow tube fixed at one end to a platform and free at the other end to wobble or rotate around an imaginary vertical axis. Each output pair of the 3-phase generator is connected to an input terminal pair of each actuator. Each actuator has a pair of terminals (one on the inside and one on the outside of the actuator). FIG. 3 illustrates this arrangement.

EXAMPLE 3

Composite Wing-flap

Figure 4:
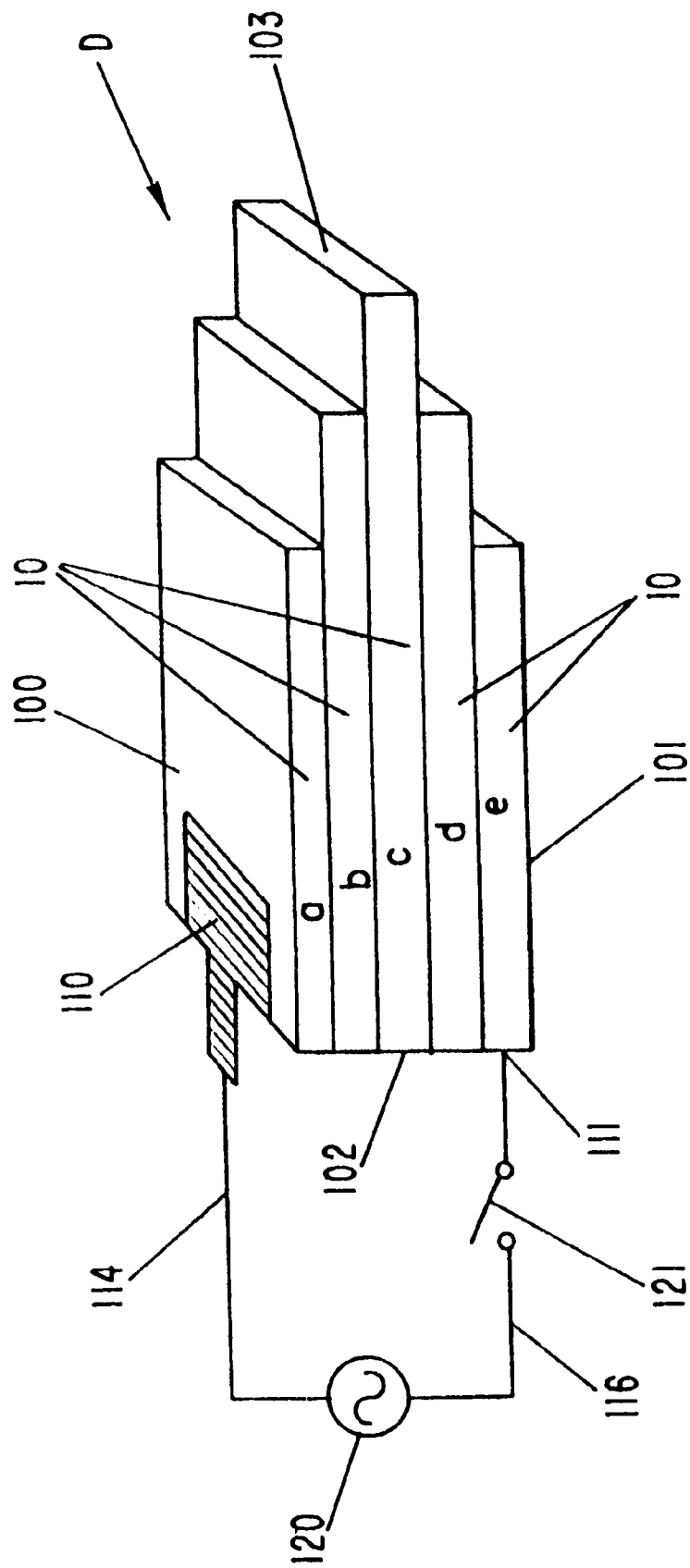
FIG. 4 is a perspective view of the actuator of the invention showing multiple, stacked treated membrane actuators in a composite structure with terminals connected to a power source at one end to be used as a composite wing-flap.

FIG. 4 is a perspective view showing multiple, treated membrane actuators in a stacked (sandwiched), configuration D which is designed to accommodate more power for specific actuations. Actuators 10a, 10b, 10c, 10d, and 10e are each independent planar actuators of different lengths (to provide different stiffness, and therefore resonant frequency, of the composite wing) manufactured according to the process of the invention and formed in a stacked configuration D which as a whole comprises a top surface 100 (shown), a bottom surface 101 (not shown), a first end 102 and a second end 103. Terminals 110 and 111 are connected to top-surface 100 and bottom surface 101, respectively, at first end 102 of actuator D. Terminals 110 (shown) and 111 (not shown) are also connected by electrical wires 114 and 116, respectively, to a power source 120. Electrical wire 116 contains an on-off switch 121. Several of these membrane actuators 10 can be assembled in series and multiple amounts of voltage applied to increase power in the composite actuator. Actuators 10a–e act as series resistor elements especially at higher frequencies.

The actuator of FIG. 4 is a resistive element by nature. Therefore, as one stacks several of the actuators, in effect one increases the overall resistance of the combined system. This in turn can allow for higher input voltages. The variation in length of each actuator is due to the desired stiffness of the wing as a whole. Since each actuator has conductivity through its thickness, there is no need to connect wires to faces. By just stacking them one can produce a thicker and more powerful actuator that can handle higher loads. The only necessary terminal connections are on the top face 100 of the top layer 10a and the bottom face 101 of the bottom layer 10e to an alternating (oscillating) source of voltage.

EXAMPLE 4

Robotic Swimming Structure

Figure 5:
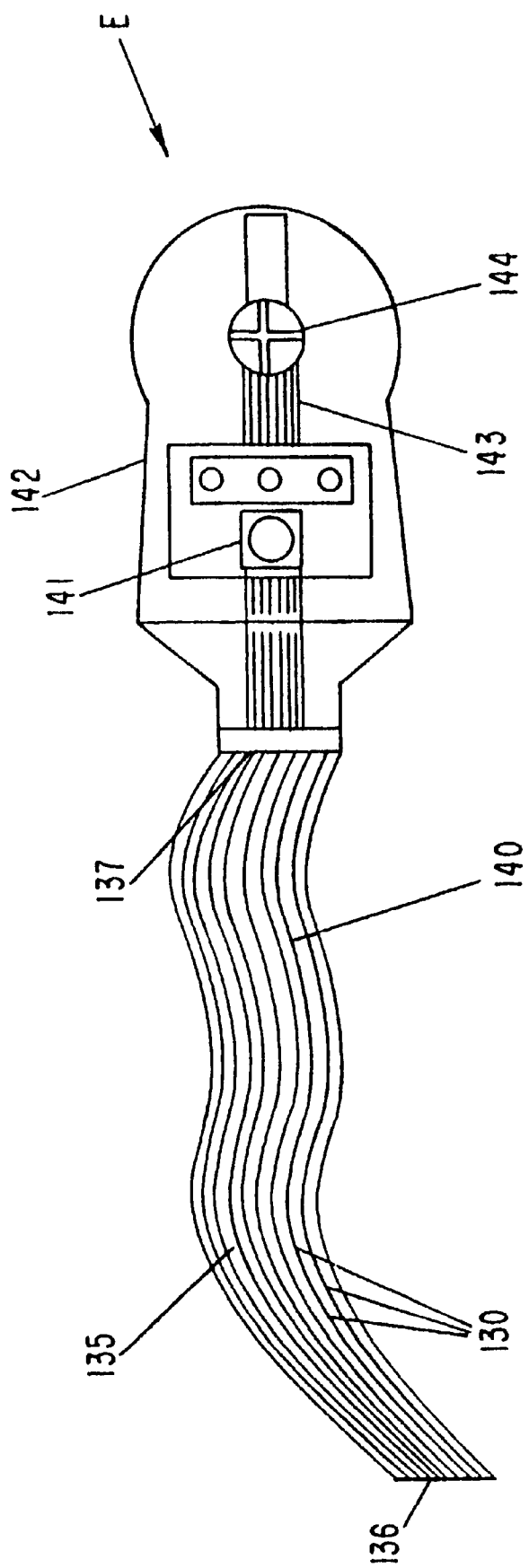
FIG. 5 is a schematic view in elevation of the actuator of the invention showing the treated membrane actuator in elastic form with imprinted electrodes for use as a robotic swimming structure. The membrane is connected to an electronic guidance and control system at one end.

FIG. 5 shows one embodiment of a robotic swimming structure made by cutting and packaging strips of treated ion-exchange membranes 130 to desired size and shape and consequently placing an alternating low voltage (1.5–2.5 V-peak per strip) across the muscle assembly E as shown. In this Figure, muscle assembly E is formed of said polymer gel strips 130 which may be encapsulated into an elastic membrane 135 with electrodes 140 (not shown) imprinted on each strip therein and with a first end 136 (free) and a second end 137 (fixed). Second end 137 is attached to an appropriate electronics and wiring structure 141 for providing guidance and control to actuate the muscle assembly E. Structure 141 as shown comprises a sealed housing module 142 containing therein a means for generating a signal 143 and a means for generating power 144. The tail assembly consists of electrically actuated artificial muscles such as ion-exchange membranes cut in tiny fibers or strips. The tail is then encapsulated in an elastic membrane. The ends of fibers closer to the head assembly 142 are wired to a miniature printed circuit board (PCB) or like assembly to a signal generator assembly consisting of an oscillator circuit and batteries or other power source. The head assembly is preferably sealed to protect the circuitry and electronics from the elements.

By varying the frequency of the applied voltage to the membrane muscle, the speed of muscle-bending oscillation of muscle assembly E, and therefore propulsion of the swimming structure, can be modulated. In this manner, robotic swimming fishes and submarine structures containing a sealed signal and power-generating module (preferably in the head assembly) can be made to swim at various depths by varying the buoyancy of the structure by conventional means. Remote commands via radio signals can then be sent to modulate propulsion speed and buoyancy by radio controls.

EXAMPLE 5

Robotic Fish

Figure 6:
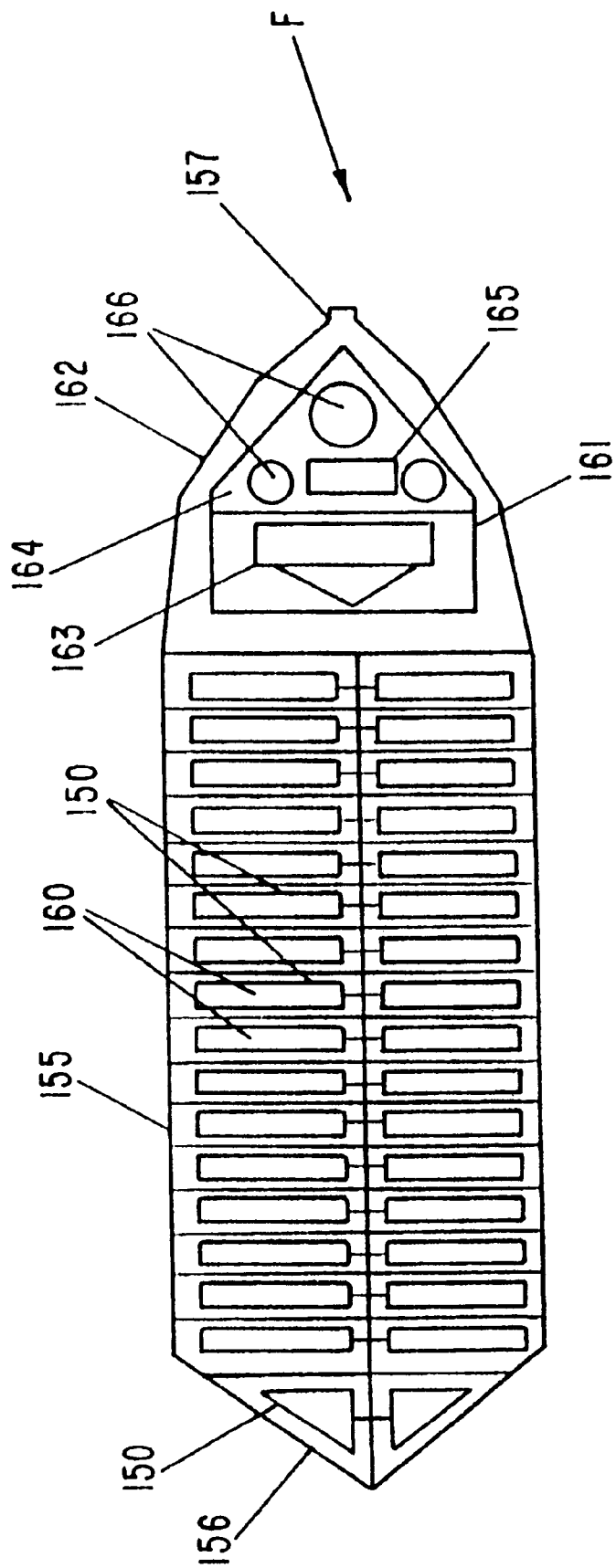
FIG. 6 is a plan view from the top of the actuator of the invention showing the treated membrane actuator imprinted with multiple electrodes spaced throughout and formed in a single rigid structure with the power source at one end. The actuator packaged In this form is suitable for use as a robotic fish.

FIG. 6 is a plan view of the actuator of the invention showing another embodiment of the treated membrane actuator in a elastic construction with imprinted electrodes for use as a robotic swimming structure, more specifically a robotic fish. FIG. 6 shows a robotic swimming structure made by cutting and packaging strips of treated ion-exchange membranes 150 in two rows of desired size and shape and imprinted with electrodes 160 spaced throughout and in a single structure. In this Figure, muscle assembly structure F is formed of said polymer gel strips 150 that may be encapsulated into an elastic membrane 155 with multiple electrodes 160 imprinted therein and with a first end 156 (tail) and a second end 157 (head). Head assembly 157 contains appropriate electronics and wiring structure 161 for providing power, guidance and controls to the muscle assembly F. Structure 161 is contained in a sealed housing module 162, containing therein a means for generating a signal 163 and a means for generating power 164. The power source 164 at end 157 places an alternating low voltage (1.5–2.5 V-peak per strip) across the muscle assembly F as shown. Power source 164 includes an erasable, programmable (EPROM) chip 165 and batteries 166. Note the two rows of small actuators in parallel. Each has two terminals that are connected individually to the multi-phase signal generator 163 located in the head assembly 157. There are also batteries (or other power source) housed in this section for required voltage input. By energizing one pair (across) of actuators at a time and then the consequent pairs downstream, one can produce a propagating or traveling wave downstream on each side of the fish. This will produce a sting-ray type of motion which propels the swimming structure forward. The middle terminals or spines act as conductors that connect the signal generator outputs in the head assembly to each actuator in the tail or wing assembly.

By varying the frequency of the applied voltage, the speed of muscle-bending oscillation of the membranes 150, and therefore propulsion of the swimming structure F, can be modulated. In this manner, robotic swimming fishes and submarine structures containing a sealed signal and power-generating module (preferably in the head assembly) can be made to swim at various depth by varying the buoyancy of the structure by conventional means. Remote commands via radio signals can then be sent to modulate propulsion speed and buoyancy by radio controls.

EXAMPLE 6

Resonant Flying Machine

Figure 7:
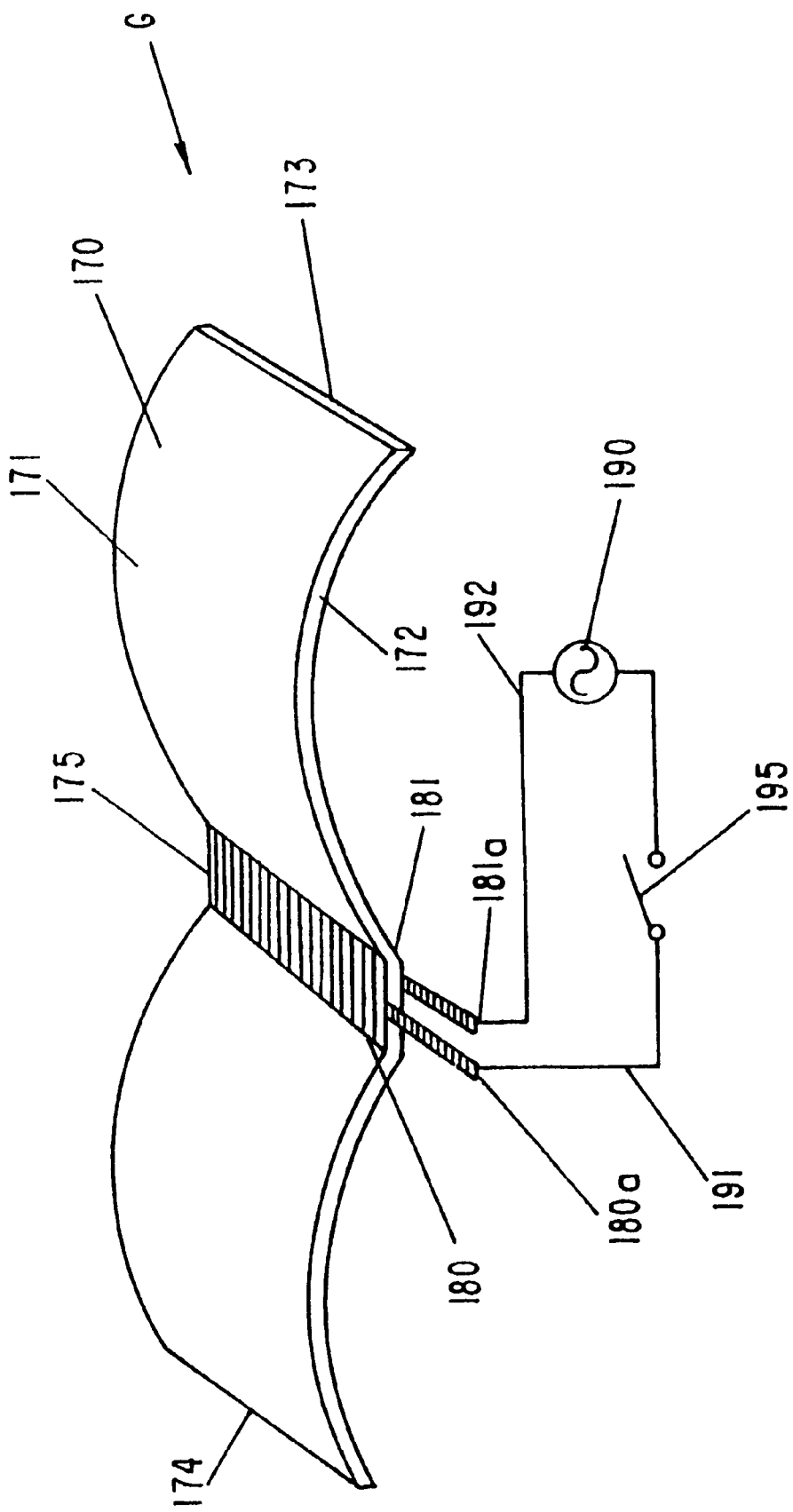
FIG. 7 is a perspective view of the actuator of the invention showing the treated membrane actuator with terminals extending through a central axis of the membrane and connected to a power source. The membrane is packaged in this form for application as a resonant flying machine.

FIG. 7 is a perspective view of the actuator of the invention showing a flying machine G constructed from treated membrane actuator 170 formed in a single sheet having a top surface 171 (shown), a bottom surface 172 (not shown), a first end 173, a second end 174 (not shown) and a central axis 175. Terminal 180, attached to top surface 171, extends along the central axis 175 of the membrane 170 equidistant from first end 173 and second end 174, and diametrically opposed terminal 181 (not shown), attached to bottom surface 172, extends along the central axis 175 of the membrane 170 equidistant from first end 173 and second end 174. Terminals 180 and 181 are connected at their ends 180a and 181a to a power supply 190 by electric wires 191 and 192 respectively. As shown, wire 191 connecting terminal 180 to power supply 190, includes an on-off switch 195.

The membrane is packaged in this form for application as a resonant flying machine. In this configuration, the treated membranes ("muscles") can flap like a pair of wings and create a flying machine. "Resonant" means excitation at the resonant frequency of the membrane, which causes the most violent vibration of the membrane. Each body of mass has a resonant frequency at which it will attain its maximum displacement when shaken by some input force or power. To obtain large displacements of the actuator, one should apply oscillating signals at a frequency close to its body resonant frequency.

In FIG. 7 one sees a large actuator strip with a pair of electrodes (terminals) in the middle fixed to the actuator surfaces of top and bottom. By connecting the circuit to an AC-power source (alternating current signal generator), one can produce oscillating motion of the membrane actuator similar to a hummingbird's or insect's wing-flap motion. Furthermore, if one applies the input voltage signal at or near the resonant frequency of the wing structure, large deformations can be obtained which will vibrate the wing structure in a resonant mode. The wing assembly is preferably encapsulated in a thin elastic membrane to prevent dehydration of the actuator.

EXAMPLE 7

Surgical Tool

The actuator can also be used as a guide wire or a micro-catheter in biomedical applications for intra-cavity endoscopic surgery and diagnostics. Small internal cavities In the body can be navigated by using these membrane actuators when used in small strips.

EXAMPLE 8

Metering Valves

Metering valves may be manufactured from the membrane of the invention, the size of an inside dimension plus required tolerances, for any tube that will permit control of aqueous fluid flow by varying the degree of bending displacement of the membrane and applying a calibrated amount of direct current.

EXAMPLE 9

Bellows Pumps

Bellows pumps can be made by attaching two planar sections of slightly different sizes of membrane sections and properly placing electrodes on the resulting cavity. This gives rise to modulating the volume trapped between the membranes when the applied voltage amplitude and frequency is set properly in order to control the flow and volume of fluid being pumped.

EXAMPLE 10

Peristaltic Pumps

Peristaltic pumps can be made from tubular sections of the membrane of the invention and placement of the electrodes in appropriate locations. Modulating the volume trapped in the tube is possible by applying appropriate input voltage at the proper frequency.

EXAMPLE 11

Microelectromechanical Systems

A variety of microelectromechanical systems (MEMS) can be made by packaging and fabricating the membranes of the present invention in small, miniature, and micro sizes. Some examples include biomedical applications such as active microsurgical tools as well as biomimetics such as micro-propulsion engines for material transport in liquid media. Other applications will involve micro-pumps, micro-valves, and micro-actuators. Flagella and cilia type actuators fall under this category.

EXAMPLE 12

Electromechanical Relay Switches

Non-magnetic, self-contained, electromechanical relay switches can be made from the membranes of the present invention by incorporating their bending characteristics in small applied voltages lo close a circuit because they are also good conductors. In this manner, several of these actuators can be arranged to make a multipole-multithrow relay switch.

EXAMPLE 13

Artificial Smooth Muscle Actuators

Artificial smooth muscle actuators similar to biological smooth muscles can be made by attaching several segments of tubular sections from membranes of the present invention and employing a simple control scheme to sequentially activate each segment to produce a traveling wave of volume change in the combined tube sections. This motion can be used to transport material or liquid contained in tube volume. The activation of each segment is similar to the peristaltic pump, above. Artificial veins, arteries, intestines made with the membrane of the present invention can be fabricated and packaged in variety of sizes depending on the application.

EXAMPLE 14

Artificial Sphincter and Ocular Muscles

Artificial sphincter and ocular muscles can also be made from the membrane of the present invention by incorporating thin strips of the actuators in a bundle form similar to the parallel actuator configuration. A typical application is in treatment of incontinence.

EXAMPLE 15

Artificial Ventricular or Cardiac-Assist Muscles

Artificial ventricular assist type muscles can also be made for heart patients with heart abnormalities associated with cardiac muscle functions.

EXAMPLE 16

Continuous Variable Aperture Mirrors and Antenna Dishes

Continuous variable aperture mirrors and antenna dishes can be made by cutting circular sections of the membrane of the present invention and placing electrodes at strategic locations. The focal point of the resulting parabolic dish can be varied by strategic placement of the electrodes and varying the amplitude of the applied voltage.

EXAMPLE 17

Linear Actuators

Linear actuators can be made to produce a variety of robotic manipulators including platform type or parallel platform actuators.

EXAMPLE 18

Slithering Device

Snake-like locomotion can be accomplished by arranging proper segments of the membrane of the invention in series and controlling each segment's bending by applying sequential input power to each segment in a cascade mode.

EXAMPLE 19

Parts Orientation/Feeding

Soft parts orientors or feeders for delicate handling of parts in a manufacturing assembly line can be made from flaps made out of the membrane of the invention.

EXAMPLE 20

Incontinence Assist Devices

Various configurations of the muscles of the invention may be used in medical applications involving incontinence. In these systems, a patient can activate the muscles by means of a push-button switch, or the like, to prevent leakage and control discharge by pressing tie switch, which is preferably battery operated.

Although the invention has been described in detail with particular reference to these preferred embodiments, other embodiments can achieve the same results. Variations and modifications of the present invention will be obvious to those skilled in the art, and it is intended to cover in the appended claims all such modifications and equivalents. The entire disclosures of all references, applications, patents, and publications cited above, are hereby incorporated by reference.

What is claimed is:

1. A method of preparing an actuator comprising the steps of:
   a) coating a bendable ion-exchange material with a substance which undergoes chemical reduction in the presence of a reducing agent;
   b) reducing the coating on the ion-exchange material by exposing the ion-exchange material to a reducing agent; and
   c) performing a secondary reduction by exposing the ion-exchange material simultaneously to a salt and a reducing agent.

2. An actuator comprising a treated ion-exchange material capable of a completely reversible deflection and means operably connected to said ion-exchange material for electrically driving the deflection of said ion-exchange material, wherein said actuator is capable of a maximum deflection of at least 15% of its length.

3. An actuator for use in a gripper mechanism comprising:
   at least two actuators comprising an ion-exchange material positioned opposite to each other and being capable of bending in equal and opposing directions, and each of said actuators having a first end;
   means for providing power to said actuators to drive the mechanical bending of said actuators in opposing directions;
   means, operably attached to said first end of each of said actuators, for conducting electrical impulses across said actuators; and
   wiring means, operably attached to said conducting means and to said means for providing power, for electrically connecting said actuators to said power source.

4. An actuator for providing three-dimensional movement, comprising:
   three actuators comprising an ion-exchange material and comprising a hollow triangular tube having a longitudinal axis and a first end wherein each of said actuators of said tube comprises a face of said tube;
   means, operably attached to said first end of each of said actuators, for conducting a signal across each of said faces of said tube, thereby stimulating each face of said tube at a phase angle apart from each adjacent face to produce a motion around said longitudinal axis of said tube; and
   means for providing power to said signal conducting means; and
   tube to said power means, attached to said signal conducting means, for operably connecting said tube to said power providing means.

5. An actuator for use as a wing flap, comprising:
   at least two actuators comprising a bendable ion-exchange material sandwiched in series in a stack configuration, each of said actuators formed in a planar layer and capable of acting as a series resistor element and said stack having first and second ends, a top surface and a bottom surface;
   means, operably attached to said stack at said first end and said top and bottom surfaces, for conducting power across said stack;
   means for supplying power to said stack; and
   means for connecting said power supplying means to said power conducting means.

6. An actuator for use as a robotic swimming structure, comprising:
- at least two actuators formed in a bendable ion-exchange material having a first end, said ion-exchange material comprising a plurality of polymer gel fibers imprinted with means for conducting power through said ion-exchange material;
- means, operably attached to said ion-exchange material at said first end, for conducting an alternating low voltage across said ion-exchange material;
- means for providing power to said conducting means;
- means for modulating speed of bending of said ion-exchange material varying the frequencies of the applied voltage; and
- means for operably connecting said conducting means to said power providing means.

7. An actuator for use as a resonant flying machine, comprising:
- at least one ion-exchange material actuator in the form of a planar layer having first and second ends, a top surface and a bottom surface;
- means for conducting power across said ion-exchange material actuator, operably attached to said top and bottom surfaces of said ion-exchange material and along a central axis of said ion-exchange material equidistant from said first and second ends, whereby said ion-exchange material actuator is capable of reversibly bending in a flapping motion upon receiving power;
- means for providing power to said conducting means; and
- means for connecting said conducting means to said power providing means.

8. An actuator for use as a guide wire in medical applications, comprising:
- at least one bendable ion-exchange material actuator formed in a strip;
- means for providing power to said strip; and
- means for connecting said strip to said power supply.

9. An actuator comprising:
- a bendable ion-exchange material; and
- a coating on said ion-exchange material which has undergone chemical reduction in the presence of a reducing agent and a secondary reduction in the simultaneous presence of a reducing agent and a salt.

10. The actuator of claim 2 wherein said actuator is capable of a maximum deflection of at least 55% of its length.

11. The actuator of claim 2 wherein said actuator is capable of a maximum deflection of up to 75% of its length.

* * * * *